United States Patent [19]

Hughes

[11] 4,453,542

[45] Jun. 12, 1984

[54] VORTEX-GENERATING MEDICAL PRODUCTS

[75] Inventor: Nathaniel Hughes, Palm Springs, Calif.

[73] Assignee: Vortran Corporation, Beverly Hills, Calif.

[21] Appl. No.: 213,843

[22] Filed: Dec. 8, 1980

[51] Int. Cl.$^3$ .................... A61M 11/02; B05B 17/06
[52] U.S. Cl. ........................ 128/200.21; 239/405; 239/338; 239/406
[58] Field of Search .............. 128/200.18, 200.21, 128/200.14; 239/102, 405, 4, 306–310, 406, 463; 261/DIG. 65

[56] References Cited

U.S. PATENT DOCUMENTS

| | | | |
|---|---|---|---|
| 756,161 | 3/1904 | Farmer | 128/200.21 |
| 2,826,454 | 3/1958 | Coanda | 128/200.18 |
| 4,109,862 | 8/1978 | Hughes | 239/102 |
| 4,190,203 | 2/1980 | Hughes | 239/102 |
| 4,195,044 | 3/1980 | Miller | 128/200.21 |
| 4,241,877 | 12/1980 | Hughes | 239/405 |

FOREIGN PATENT DOCUMENTS 452965 11/1949 Italy ........................... 128/200.21

Primary Examiner—Kyle L. Howell
Assistant Examiner—Karin M. Reichle
Attorney, Agent, or Firm—Christie, Parker & Hale

[57] ABSTRACT

A nebulizer comprises an upright, cylindrical, tower-like chamber mounted on the lid of a liquid storage bottle and a vortex-generating transducer. The chamber has a closed upper end and an open lower end directed to the bottle. The transducer is mounted on the closed end with its outlet opening into the chamber. Windows are formed in the side of the chamber adjacent the outlet of the transducer. A nebulizer comprises a T-shaped chamber secured to the inside of a closed liquid storage bottle and a vortex-generating transducer. The chamber has inline legs with open ends and a transverse leg with a closed end. One open end faces downwardly into the bottle, the other open end is connected by an elbow to a spout leaving the bottle. The transducer is mounted on the closed end with its outlet facing into the chamber and its axis is pointed down at a small acute angle to the axis of the transverse leg.

1 Claim, 13 Drawing Figures

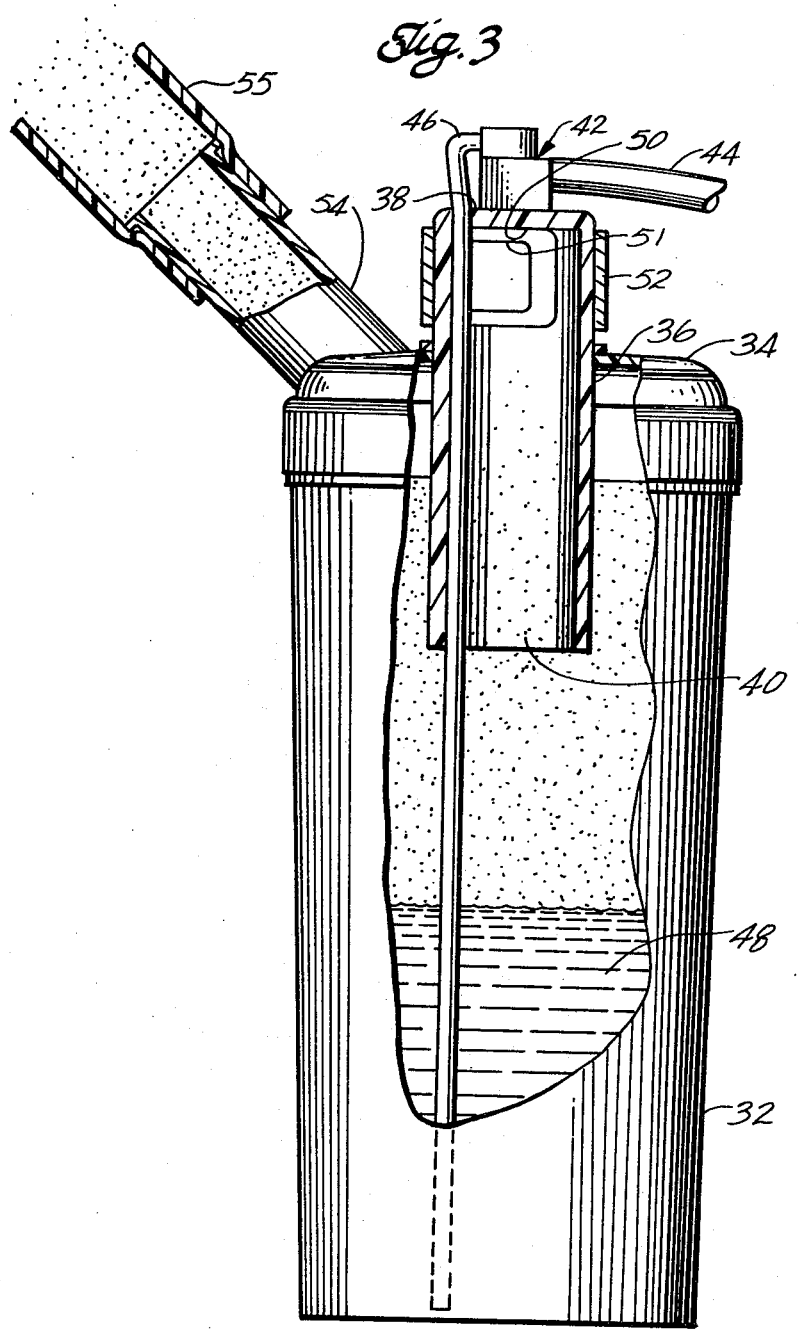

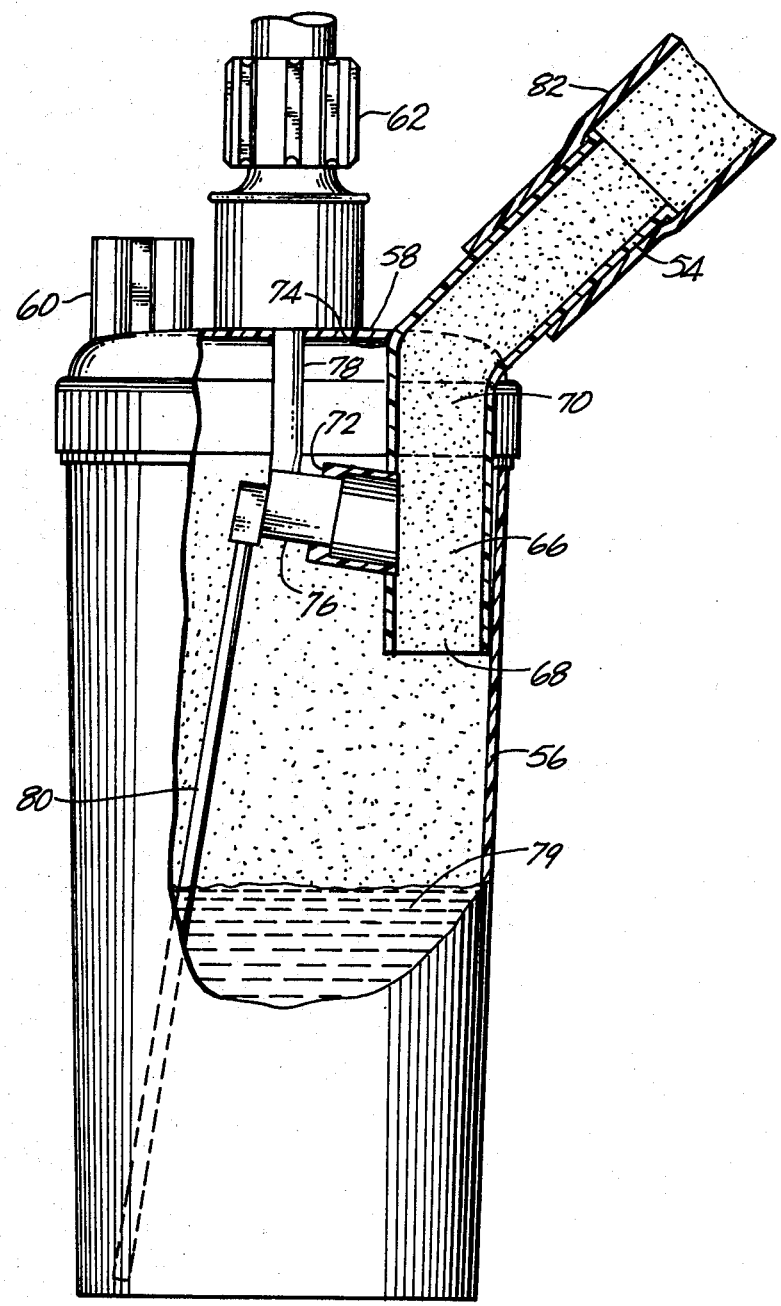

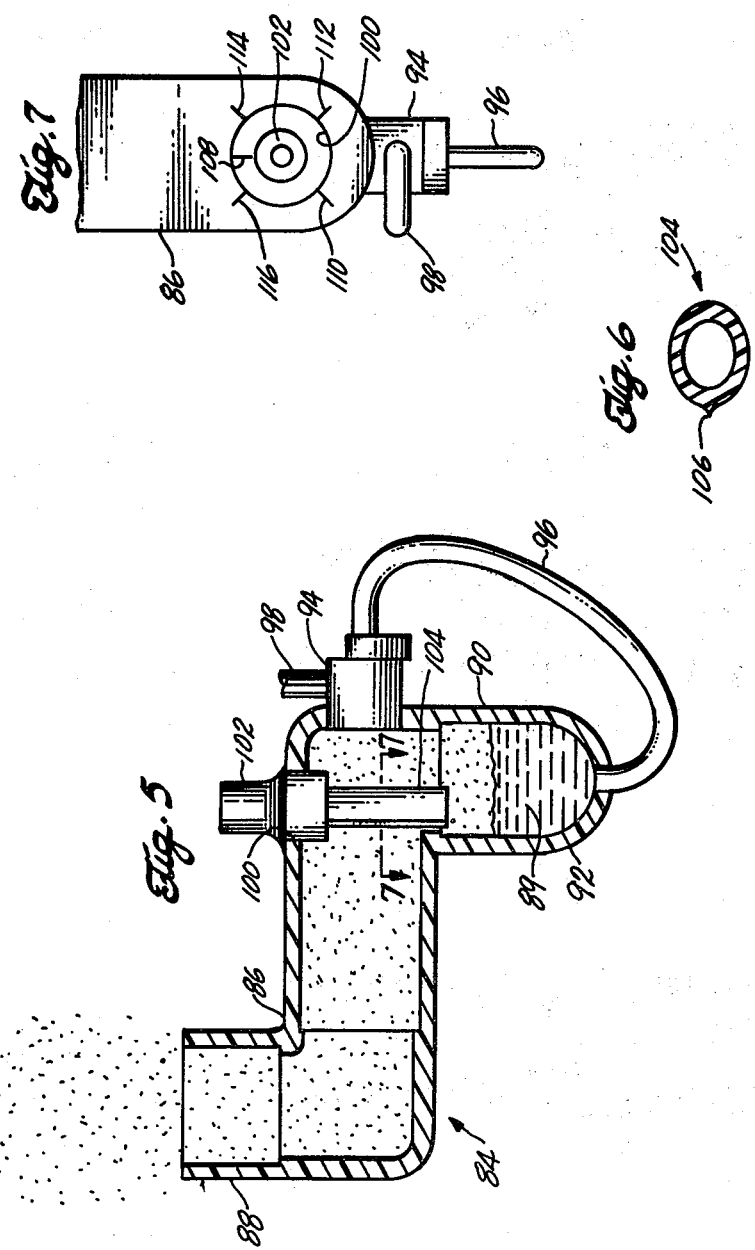

VORTEX-GENERATING MEDICAL PRODUCTS

BACKGROUND OF THE INVENTION

This invention relates to fluid flow devices and, more particularly, to vortex-generating medical products.

My co-pending application Ser. No. 951,621, filed Oct. 16, 1978, now U.S. Pat. No. 4,241,877 and U.S. Pat. Nos. 4,109,862 and 4,190,203 disclose vortex-generating devices that effectively atomize liquid. My U.S. Pat. No. 4,240,293, which is to issue on Dec. 23, 1980, discloses vortex-generating devices used as flowmeters.

Medical products such as nebulizers, humidifiers, and inhalers function as atomizers; and medical products such as spirometers function as flowmeters.

SUMMARY OF THE INVENTION

According to the invention, vortex-generating devices are incorporated into improved medical products.

One aspect of the invention is a nebulizer comprising an upright, cylindrical, tower-like chamber mounted on the lid of a liquid storage bottle and a vortex-generating transducer. The chamber has a closed upper end and an open lower end directed into the bottle. The transducer is mounted on the closed end with its outlet opening into the chamber. A gas, namely oxygen, is fed to the gas inlet of the transducer. Liquid from the container is fed to the liquid inlet of the transducer. Atmospheric air is drawn into the chamber through windows in its side adjacent the outlet of the transducer. The chamber serves to amplify the vorticity of the gas leaving the outlet of the transducer and thereby further atomize the liquid. Finely atomized liquid in an air-oxygen mixture exits from a spout in the lid.

Another aspect of the invention is a nebulizer comprising a T-shaped chamber secured to the inside of a closed liquid storage bottle and a vortex-generating transducer. The chamber has inline legs with open ends and a transverse leg with a closed end. One open end faces downwardly into the bottle, the other open end is connected by an elbow to a spout leaving the bottle. The transducer is mounted on the closed end with its outlet facing into the chamber and its axis is pointed down at a small acute angle to the axis of the transverse leg. A source of gas, namely oxygen, is fed to the gas inlet of the transducer and liquid stored in the bottle is fed to the liquid inlet of the transducer.

Another aspect of the invention is a mist inhaler comprising a chamber and a vortex-generating transducer opening into the chamber. A gas under pressure is fed to the air inlet of the transducer and liquid stored in the chamber is fed to the liquid inlet of the transducer. A rotatable air foil is disposed in front of the transducer outlet. The mist density is dependent on the orientation of the air foil.

Another aspect of the invention is a flowmeter comprising a passage with a cylindrical restriction and a pressure-sensing probe extending into the restriction in a plane transverse to the direction of flow. Preferably, the passage has cylindrical chambers upstream and downstream of the restriction, a converging section connecting the upstream chamber to the restriction, and a diverging section connecting the restriction to the downstream chamber. In one embodiment, a rod which is thicker than the probe, extends diametrically across the flow passage; the rod is either longitudinally aligned with the probe or transverse thereto. In another embodiment, an additional pressure-sensing probe, preferably chambered, is disposed between the rod and the other probe.

BRIEF DESCRIPTION OF THE DRAWINGS

The features of specific embodiments of the best mode contemplated of carrying out the invention are illustrated in the drawings, in which:

FIG. 3 is a side, partially sectional view of a nebulizer incorporating principles of the invention;

FIG. 4 is a side, partially sectional view of a humidifier incorporating principles of the invention;

FIG. 5 is a side, partially sectional view of an inhaler incorporating principles of the invention;

FIG. 6 is a sectional view of the air foil in the inhaler of FIG. 5;

FIG. 7 is a top plan view of part of the inhaler of FIG. 5;

DETAILED DESCRIPTION OF THE SPECIFIC EMBODIMENTS

Figure 1:
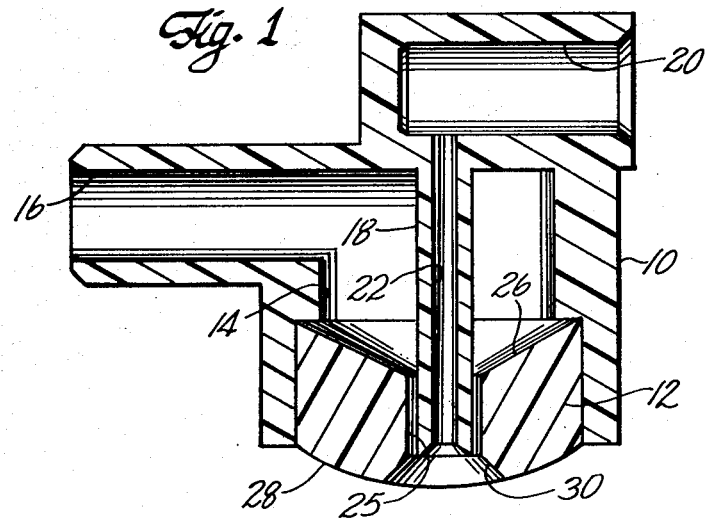
FIG. 1 is a side-sectional view of a vortex-generating transducer used to practice the invention.
Figure 2:
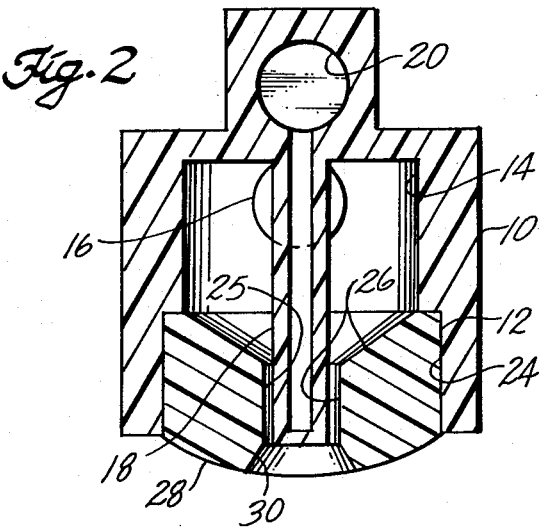
FIG. 2 is a front-sectional view of the transducer of FIG. 1.
Figure 8:
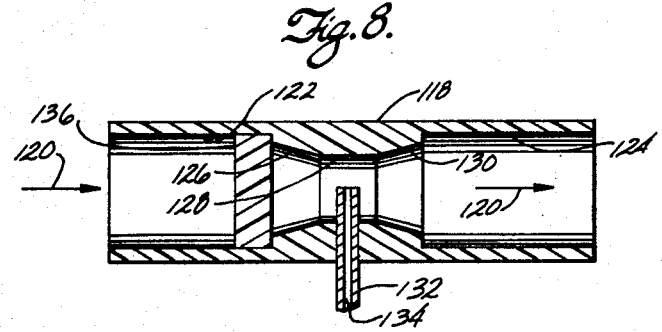
FIGS. 8 and 9 are side-sectional and end-sectional views, respectively, of a flowmeter incorporating principles of the invention.
Figure 9:
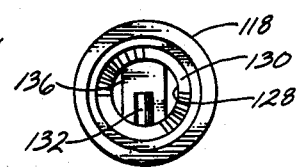
Figure 10:
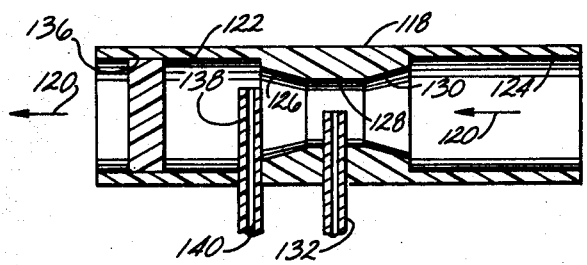
FIGS. 10 and 11 are side-sectional and end-sectional views of another embodiment of a flowmeter incorporating principles of the invention.
Figure 11:
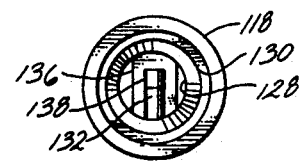
Figure 12:
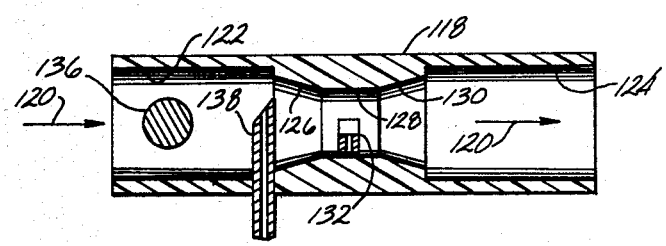
FIGS. 12 and 13 are side-sectional and end-sectional views, respectively, of still another embodiment of a flowmeter incorporating the principles of the invention.
Figure 13:
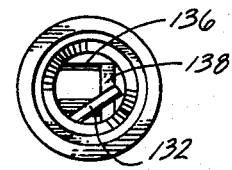

In FIGS. 1 and 2, a vortex-generating transducer comprises a body member 10 and an insert 12, which are preferably injection-molded parts. A large cylindrical bore 14 and a small cylindrical bore 16, which opens into bore 14, are formed in body member 10. Bores 14 and 16 lie on intersecting orthogonal axes. Body member 10 includes a hollow, cylindrical rod 18 that extends the length of bore 14 in axial alignment therewith. A small cylindrical bore 20 is formed in body member 10 behind rod 18. Bores 16 and 20 lie on parallel axes. A bore 22 extends through rod 18 from bore 20 to the exterior end of bore 14.

A counterbore 24 is formed in bore 14 at its exterior end. Insert 12 fits into counterbore 24, where it is cemented in place. A cylindrical bore 25, which has a slightly larger diameter than rod 18, is formed in insert 12. Rod 18 extends through bore 25 in axial alignment therewith to form therebetween a small annular passage. The interior end of insert 12 has a conical concavity 26 and the exterior end thereof has a spherical convexity 28. A conical concavity 30 is formed between the center of convexity 28 and bore 25.

In operation, a source of gas under pressure is connected to bore 16, which serves as a gas inlet, and a source of liquid is connected to bore 20, which serves as a liquid inlet. Bore 14 serves as a main flow passage. The main flow passage has a large annular, upstream portion formed by bore 14 and rod 18, a converging portion formed by concavity 26, a restricted annular portion formed by rod 18 and bore 25, and a diverging portion formed by concavity 30. Concavity 30 serves as the outlet. When gas entering the inlet impinges upon rod 18, vortices are generated. The gas flows in a vortical path through bore 25 to the outlet, where a low pressure is produced by the vorticity. As a result, liquid is drawn through bores 20 and 22 and is atomized by the vortically flowing gas at the open end of bore 22.

Typical dimensions for the described transducer are as follows:

| | |
|---|---|
| Length of bore 14 | .170 inch |
| Diameter of bore 14 | .312 inch |
| Length of rod 18 | .410 inch |
| Diameter of rod 18 | .066 inch |
| Diameter of bore 22 | .054 inch |
| Diameter of bore 16 | .125 inch |
| Diameter of bore 25 | .730 inch |
| Length of bore 25 | .730 inch |
| Included angle of concavity 26 | 60° degrees |
| Included angle of concavity 30 | 45° degrees |
| Radius of convexity 28 | .350 inch |
| Diameter of bore 20 | .125 inch |
| Base diameter of concavity 26 | .312 inch |
| Base diameter of concavity 30 | .130 inch |

In FIG. 3, a nebulizer comprises a bottle 32 having a screw-on lid 34. An upright cylindrical tower-like chamber 36 is mounted on lid 34. Chamber 36 has a closed upper end 38 outside bottle 32 and an open lower end 40 inside bottle 32. Chamber 36 passes through an opening in lid 34 between ends 38 and 40. A vortex-generating transducer 42 is mounted on end 38 with its outlet opening into chamber 36. The main flow passage of transducer 42 is axially aligned with chamber 36. Transducer 42 could be the transducer disclosed in FIGS. 1 and 2 or one of the vortex-generating devices disclosed in my co-pending application Ser. No. 951,621, filed Oct. 16, 1978, now U.S. Pat. No. 4,241,877 or my U.S. Pat. No. 4,189,101, issued Feb. 19, 1980, the disclosures of which are incorporated fully herein by reference. A source of gas under pressure, namely oxygen, is connected by a tube 44 to the gas inlet of transducer 42. A tube 46 connects the bottom of bottle 32 to the liquid inlet of transducer 42. Tube 46 enters bottle 32 through end 38. A liquid, namely sterilized water, which is represented by a reference numeral 48, is stored in bottle 32. The open end of tube 46 is below the level of water 48. A pair of windows 50 are formed on diametrically opposite sides of the wall of chamber 36 between transducer 42 and lid 34. The effective area of windows 50 is adjusted by positioning a slide 52 to cover partially windows 50. Slide 52 has diametrically opposite openings 51 through which air passes into chamber 36. A spout 54 is formed in lid 34 at an acute angle to the horizontal, e.g., 45°, to serve as an outlet from the nebulizer. A tube 55 is connected from spout 54 to a patient receiving respiratory care or treatment.

In operation, oxygen fed to the gas inlet passes through transducer 42 generating vorticity therein and water 48 is drawn through tube 46 into transducer 42 where it is atomized by the vortically moving oxygen. The water-carrying oxygen moves down through chamber 36 in a vortical path entraining air from the atmosphere drawn in through windows 50. As the oxygen, atmospheric air, and water flow downwardly toward open end 40, the axial velocity is converted to vorticity, thereby amplifying the vorticity and further atomizing the water. Finely atomized water thus flows out of the bottom of chamber 36, fills the top of bottle 32, and exits through spout 54. Large water particles return to the mass of water 48 in bottle 32, leaving only the finely atomized particles in the in the oxygen-air mixture above the water level. For example, in one embodiment of the described nebulizer, it was found that more than 90% of all the water particles leaving bottle 32 were less than one micron at an oxygen concentration of 28% and virtually no particles were larger than five microns. The oxygen concentration can be varied over a wide range, e.g., 26% or less, up to 100%, by positioning slide 52. The described nebulizer produces finely atomized water particles over a wide range of oxygen concentration. Significantly, the mist exiting spout 54 has a higher temperature than the ambient air and little water collects in tube 55.

Typical dimensions for the nebulizer are as follows:

| | |
|---|---|
| Inside diameter of chamber 36 | 1.2 inches |
| Length of chamber 36 | 3.64 inches |
| Spacing of the outlet of transducer 42 from end 32 | 0.32 inch |
| Height of bottle 32 | 6 inches |
| Diameter of bottle 32 | 2.75 inches |
| Dimensions of windows 50 | 0.6 inch × 0.6 inch |

In FIG. 4, a humidifier comprises a bottle 56 and a screw-on lid 58. Lid 58 has a pressure relief valve 60 and an oxygen line fitting 62 of conventional construction and a spout 64 at an acute angle, e.g., 45° to the horizontal. A T-shaped chamber 66 is secured to the inside of bottle 56 below spout 54. Chamber 66 has inline legs with open ends 68 and 70 and a transverse leg with a closed end 72. Open end 68 faces downwardly. Open end 70 is connected by an elbow 74 to spout 54. A transducer 76, identical to transducer 42 in FIG. 3, is mounted on end 72 with its outlet facing into chamber 66. Transducer 76 and the transverse legs are oriented so the axis of the main flow passage and the transverse leg axis are pointed down at an angle less than 90°, e.g., 85°, to the axes of the inline legs of chamber 66. A tube 78 is connected from fitting 62 to the gas inlet of transducer 76 to supply oxygen thereto. A liquid, namely sterilized water, represented by a reference numeral 79, is stored in bottle 56. A tube 80 leads from the bottom of bottle 56 to the liquid inlet of transducer 76 to supply sterilized water thereto. A tube 82 is connected from spout 54 to a patient under respiratory care or treatment.

In operation, oxygen under pressure supplied to the gas inlet of transducer 76 forms vortices at its outlet, drawing into transducer 76 water stored in bottle 56, which is atomized. The vorticity of the water-carrying oxygen leaving the outlet of transducer 76 is amplified by the transverse leg of chamber 56. When the vortically flowing oxygen collides with the wall of chamber 56 where its inline legs meet, the water particles separate according to size, by virtue of the downward angle of transducer 76. The larger water particles fall from open end 68 back into the mass of stored water 79. The smaller particles flow upwardly in the oxygen to form a narrow band dry mist, which is delivered by tube 82 to the patient. This mist is 5° to 7° F. above the ambient air and the temperature of returning sterilized water 79 is 5° to 10° below the ambient air temperature.

Typical dimensions for the described humidifier are as follows:

Diameter of legs of chamber 66—0.610 inch

Length of transverse leg—0.640 inch

In FIG. 5, a mist inhaler comprises a chamber 84, which could be formed from two 90° elbows joined together. Chamber 84 has a long, straight section 86, an open section 88 extending at right angles to section 86 at one end, and a section 90 extending at right angles to section 86 at the other end. The end of section 90 is covered by a dish-shaped cap 92. A transducer 94, which is the same as transducer 42 in FIG. 3, is mounted in the end wall of section 84 with its outlet opening into section 84. The main flow passage of transducer 94 is at an acute angle 5° to 10° upward with section 84. A liquid 89 such as water or medication is stored in section 90. A tube 96 leads from the bottom of section 90 to the liquid inlet of transducer 94. A tube 98 leads from a source of oxygen or air under pressure to the gas inlet of transducer 94. An opening 100 is formed in the side wall of section 84 opposite section 90 and in front of the outlet of transducer 94. A rotatable plug 102 is inserted in opening 100. An air foil 104, which could comprise a piece of rubber tubing, extends from plug 102 across section 86 in front of the outlet of transducer 94. As described above, the oxygen fed to transducer 94 generates vorticity that atomizes the liquid in section 90. A hole extends through plug 102 and airfoil 104, the diameter of this hole controls the rate of expulsion of the mist produced by the device, and the oxygen concentration and mist density. In some embodiments the airfoil can be eliminated or changed in shape and together with variations of the hole diameter this can be used to control the above mentioned parameters. The resulting mist exits from the open end of section 88, where it can be inhaled by a patient. As plug 102 is rotated in hole 100 to vary the orientation of air foil 104, the density of the mist eminating from the open end of section 88 changes.

FIG. 6 depicts a cross section of air foil 104, which is oblong in shape. Along one end, a thin ridge 106 is formed in air foil 104. The control of mist density is principally due to the oblong shape of air foil 104.

In FIG. 7, which is a top view of the inhaler of FIG. 5, a mark 108 is scribed on plug 104 in alignment with ridge 106 on air foil 104. Marks 110 through 116 are scribed on section 84. When mark 108 is between marks 110 and 112, the mist density is a minimum and when mark 108 is between marks 114 and 116, the mist density is a maximum. Between marks 112 and 114, the marks 110 and 116, the mist density varies between a minimum and a maximum. A slightly larger mist density is observed when mark 108 is at mark 114 or mark 116 than when mark 108 is midway therebetween. It has been possible to change the mist density over a range as large as 4:1 by varying the orientation of the described air foil.

My co-pending application Ser. No. 109,839, filed Jan. 7, 1980, now U.S. Pat. No. 4,372,169 the disclosure of which is incorporated fully herein by reference, describes a number of flowmeters employing frustums as vortex-generating bluff bodies. It has now been discovered that rods extending into the flow passage transverse to the direction of flow can also serve as vortex-generating bodies in a flowmeter employing the principles of the above-mentioned co-pending application.

In the embodiment of FIGS. 8 and 9, fluid flows through a pipe 118 in the direction of arrows 120. Pipe 118 has a cylindrical, upstream chamber 122 and a cylindrical downstream chamber 124 that are connected by a converging section 126, a cylindrical section 128, and a diverging section 130, all smaller in diameter than chambers 122 and 124. The inlet pressure to chamber 122 is superatmospheric and chamber 124 feeds into the atmosphere. A rod 132 extends into the center of cylindrical section 128. A passage 134 through rod 132 is connected to a pressure sensor not shown. A rod 136, which is thicker than rod 132, extends diametrically across chamber 122 in longitudinal alignment with rod 132. Rod 132 has a squared off end. Rod 132 generates vortices that establish a vacuum pressure in cylindrical section 128. This pressure, which is subatmospheric, is representative of the flow rate through pipe 118. Rod 132 functions both as a vortex generator and a pressure sensing probe.

In the embodiment of FIGS. 10 and 11, the same reference numerals are used to identify the components in common with the embodiment of FIGS. 8 and 9. A rod 138 extends radially into the center of chamber 122 and beyond in longitudinal alignment with rods 132 and 136. A passage 140 through rod 138 couples chamber 122 to a pressure sensor not shown. As rod 132, rod 138 also serves as a vortex generator and a pressure sensing probe. The differential signal from the two pressure sensors provides a stronger, i.e., more amplified, indication of flow rate than the signal from the single pressure sensor in the embodiment of FIGS. 8 and 9.

In the embodiment of FIGS. 12 and 13, the same reference numerals are used to identify the components in common with the embodiment of FIGS. 10 and 11. Here rod 136 is oriented at 90° to rod 138. Rather than being squared off, as in the other embodiment, the end of rod 138 is chamfered so the upstream side is shorter than the downstream side. Rod 132 is oriented at an angle of 30° to rod 138. Rods 132 and 138 both extend along a chord of the flow passage rather than a radius, as best depicted in FIG. 13. This embodiment produces a larger signal from the pressure sensor but also presents more resistance to fluid flow than the other disclosed embodiments.

Many variations on the described embodiments can be made. For example, in the embodiment of FIGS. 8 and 9, rod 136 could be eliminated, rod 132 could extend along a chord instead of radially, and/or rod 136 could be oriented at 90° to rod 132. In the embodiment of FIGS. 10 and 11, rod 138 could be chamfered and/or rods 132 and 138 could extend along a chord.

Considering the small diameter of rods 132 and 138, a large vacuum signal is generated by the pressure sensors, which is indicative or large drag. Typical dimensions for the described flowmeters are as follows:

| | |
|---|---|
| Diameter of chambers 122 and<br>124 | .612 inch<br>.612 inch |
| Diameter of rods 132 and 138 | 0.045 inch |
| Chamfer on rod 138 | 45 degrees |
| Base diameter of section 126 | .520 inch |
| Included angle of section 126 | 45° degrees |
| Base diameter of section 130 | .520 inch |
| Included angle of section 130 | 21° degrees |
| Diameter of section 128 | .342 inch |
| Length of section 128 | .310 inch |
| Spacing between rods 132 and 138 | .400 inch |
| Spacing between rods 136 and 138 | .400 inch |

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention.

What is clamed is:

1. A nebulizer for medical purposes comprising:

a liquid storage container;

a cylindrical chamber mounted on the container, the chamber having a closed end outside the container and an open end inside the container;

a vortex generating transducer having a gas inlet, a liquid inlet, and an outlet;

means for mounting the transducer on the closed end of the chamber such that the outlet is directed towards the open end of the chamber;

window means in the side of the chamber near its closed end opening the interior of the chamber to the outside of the container;

a tube connecting the bottom of the container to the liquid inlet;

a source of gas under pressure connected to the gas inlet; and an exit from the container outside the chamber.

* * * * *